(12) United States Patent
Anumakonda et al.

(10) Patent No.: US 8,507,741 B2
(45) Date of Patent: Aug. 13, 2013

(54) METHODS FOR CO-PRODUCTION OF ALKYLBENZENE AND BIOFUEL FROM NATURAL OILS USING HYDROCRACKING

(75) Inventors: Amarendra Anumakonda, Naperville, IL (US); Srikantiah Raghuram, Buffalo Grove, IL (US); Joao Jorge da Silva Ferreira Alves, Arlington Heights, IL (US); Andrea G. Bozzano, Northbrook, IL (US)

(73) Assignee: UOP LLC, Des Plaines, IL (US)

( * ) Notice: Subject to any disclaimer, the term of this patent is extended or adjusted under 35 U.S.C. 154(b) by 131 days.

(21) Appl. No.: 13/242,825

(22) Filed: Sep. 23, 2011

(65) Prior Publication Data

US 2013/0079570 A1    Mar. 28, 2013

(51) Int. Cl.
*C07C 1/207* (2006.01)
*C07C 2/64* (2006.01)
*C07C 5/22* (2006.01)

(52) U.S. Cl.
USPC ........... 585/323; 585/314; 585/240; 585/446; 585/734

(58) Field of Classification Search
USPC .......................... 585/323, 314, 240, 446, 734
See application file for complete search history.

(56) References Cited

U.S. PATENT DOCUMENTS

| | | | |
|---|---|---|---|
| 7,776,207 B2 | 8/2010 | Abhari et al. | |
| 7,883,882 B2 | 2/2011 | Franklin et al. | |
| 7,915,460 B2 | 3/2011 | Kalnes et al. | |
| 2007/0281875 A1 | 12/2007 | Scheibel et al. | |
| 2009/0158637 A1 | 6/2009 | McCall et al. | |
| 2010/0145117 A1 | 6/2010 | Seames et al. | |
| 2011/0015459 A1 | 1/2011 | Aalto et al. | |

*Primary Examiner* — Thuan D Dang
(74) *Attorney, Agent, or Firm* — David J Piasecki

(57) ABSTRACT

Embodiments of methods for co-production of linear alkylbenzene and biofuel from a natural oil are provided. A method comprises the step of deoxygenating the natural oils to form paraffins. A first portion of the paraffins is hydrocracked to form a first stream of normal and lightly branched paraffins in the $C_9$ to $C_{14}$ range and a second stream of isoparaffins. The first stream is dehydrogenated to provide mono-olefins. Then, benzene is alkylated with the mono-olefins under alkylation conditions to provide an alkylation effluent comprising alkylbenzenes and benzene. Thereafter, the alkylbenzenes are isolated to provide the alkylbenzene product. A second portion of the paraffins and the isoparaffins are processed to form biofuel.

19 Claims, 1 Drawing Sheet

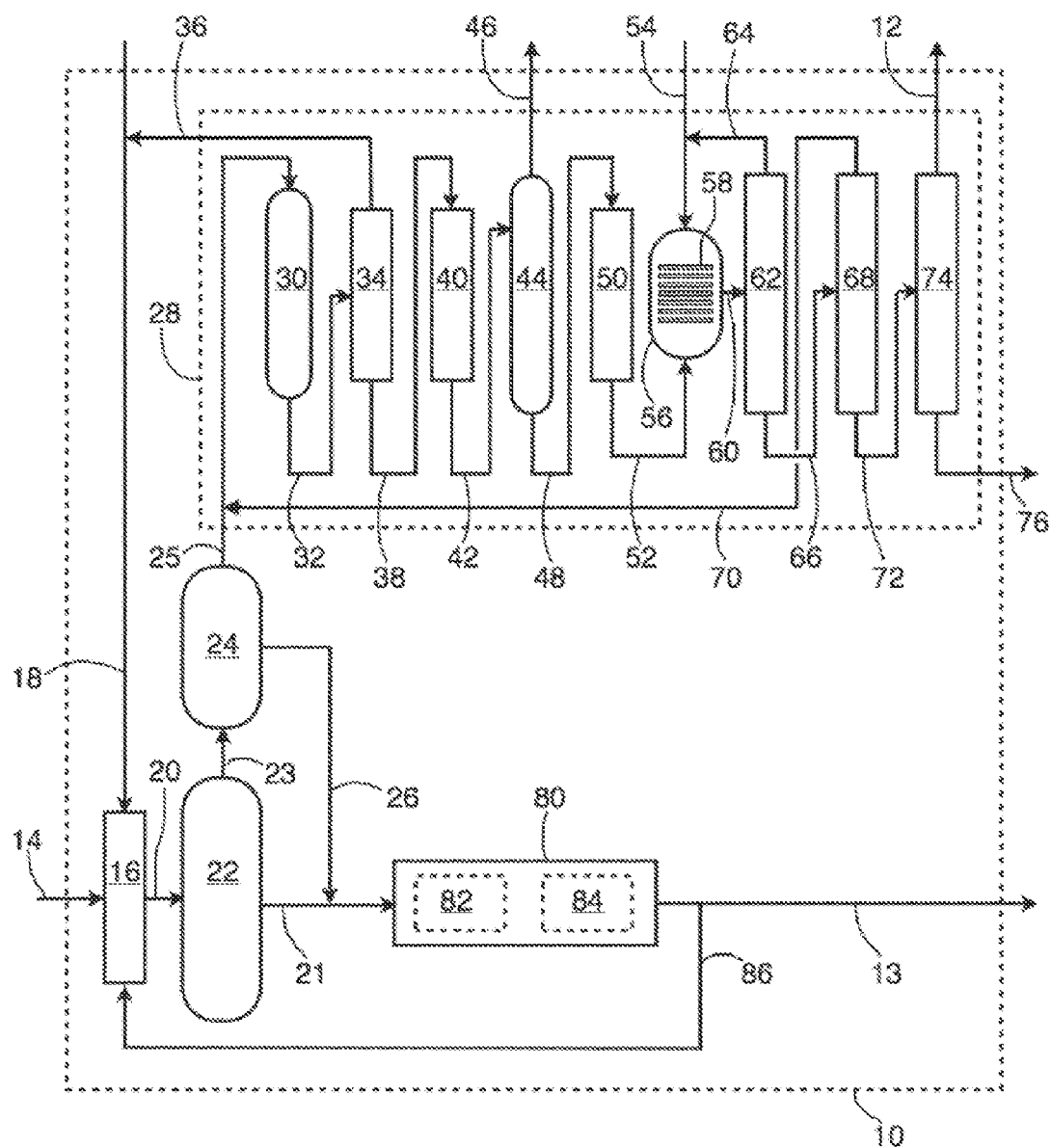

METHODS FOR CO-PRODUCTION OF ALKYLBENZENE AND BIOFUEL FROM NATURAL OILS USING HYDROCRACKING

FIELD OF THE INVENTION

The present invention relates generally to methods for co-production of alkylbenzene and biofuel using hydrocracking, and more particularly relates to methods for producing renewable alkylbenzene and biofuel from natural oils.

BACKGROUND OF THE INVENTION

Linear alkylbenzenes are organic compounds with the formula $C_6H_5C_nH_{2n+1}$. While n can have any practical value, current commercial use of alkylbenzenes requires that n lie between 10 and 16, or more specifically between 10 and 13, between 12 and 15, or between 12 and 13. These specific ranges are often required when the alkylbenzenes are used as intermediates in the production of surfactants for detergents. Because the surfactants created from alkylbenzenes are biodegradable, the production of alkylbenzenes has grown rapidly since their initial uses in detergent production in the 1960s.

While detergents made utilizing alkylbenzene-based surfactants are biodegradable, processes for creating alkylbenzenes are not based on renewable sources. Specifically, alkylbenzenes are currently produced from kerosene derived from fossil fuels. Due to the growing environmental concerns over fossil fuel extraction and economic concerns over exhausting fossil fuel deposits, there may be support for using an alternate source for biodegradable surfactants in detergents and in other industries.

There is also an increasing demand for the use of biofuels in order to reduce the demand for and use of fossil fuels. This is especially true for transportation needs wherein other renewable energy sources are difficult to utilize. For instance, biodiesel or green diesel and biojet or green jet fuels may provide for a significant reduction in the need and use of petroleum based fuels.

Accordingly, it is desirable to provide methods and systems for co-production of alkylbenzene and biofuel from natural oils, i.e., oils that are not extracted from the earth. Further, it is desirable to provide methods and systems that provide renewable alkylbenzenes and biofuels from easily processed triglycerides and fatty acids from vegetable, nut, and/or seed oils. Furthermore, other desirable features and characteristics of the present invention will become apparent from the subsequent detailed description of the invention and the appended claims, when taken in conjunction with the accompanying drawing and this background of the invention.

SUMMARY OF THE INVENTION

Methods for the co-production of an alkylbenzene product and biofuel from a natural oil are provided herein. In accordance with an exemplary embodiment, the method deoxygenates the natural oil to form paraffins. A first portion of the paraffins is hydrocracked to form a first stream of normal and lightly branched paraffins in the $C_9$ to $C_{14}$ range and a second stream of isoparaffins. The first stream is dehydrogenated to provide mono-olefins. Then, benzene is alkylated with the mono-olefins under alkylation conditions to provide an alkylation effluent comprising alkylbenzenes and benzene. Thereafter, the alkylbenzenes are isolated to provide the alkylbenzene product. A second portion of the paraffins and the isoparaffins are processed to form biofuel.

In another exemplary embodiment, a method is provided for the co-production of an alkylbenzene product and a biofuel from natural oil source triglycerides. In this embodiment, the triglycerides are deoxygenated to form a deoxygenated product comprising water, carbon dioxide, propane, a first portion of paraffins, and a second portion of paraffins. This stream is fractionated to separate first and second streams of paraffins. Then, the first stream of paraffins is hydrocracked to form a normal paraffin stream and an isoparaffins stream. The normal paraffin stream is dehydrogenated to provide mono-olefins. The mono-olefins are used to alkylate benzene under alkylation conditions to provide an alkylation effluent comprising alkylbenzenes and benzene. Thereafter, alkylbenzenes are isolated to provide the alkylbenzene product. The second stream of paraffins and the isoparaffins stream are processed to form biofuel.

In accordance with another embodiment, a method for co-production of an alkylbenzene product and biofuel from a natural oil is provided. In the method, the natural oil is deoxygenated with hydrogen to form a stream comprising paraffins. The paraffins are hydrocracked to form a normal paraffin stream and an isoparaffin stream. The normal paraffin stream is dehydrogenated to provide mono-olefins and hydrogen. According to the exemplary embodiment, the hydrogen provided by dehydrogenation is recycled to deoxygenate the natural oils. The mono-olefins are used to alkylate benzene under alkylation conditions to provide an alkylation effluent comprising alkylbenzenes and benzene. Then, the alkylbenzenes are isolated from the effluent to provide the alkylbenzene product. The isoparaffins stream is processed to form biofuel.

BRIEF DESCRIPTION OF THE DRAWING

Embodiments of the present invention will hereinafter be described in conjunction with the following drawing FIGURE wherein:

FIG. 1 schematically illustrates a system for co-production of alkylbenzene and biofuel in accordance with an exemplary embodiment.

DETAILED DESCRIPTION

The following Detailed Description is merely exemplary in nature and is not intended to limit the invention or the application and uses of the invention. Furthermore, there is no intention to be bound by any theory presented in the preceding Background or the following Detailed Description.

Various embodiments contemplated herein relate to methods and systems for co-production of an alkylbenzene product and biofuel from natural oils. In FIG. 1, an exemplary apparatus 10 for producing an alkylbenzene product 12 and biofuel 13 from a natural oil feed 14 is illustrated. As used herein, natural oils are those derived from plant or algae matter, and are often referred to as renewable oils. Natural oils are not based on kerosene or other fossil fuels. In certain embodiments, the natural oils include one or more of coconut oil, babassu oil, castor oil, canola oil, cooking oil, and other vegetable, nut or seed oils. The natural oils typically comprise triglycerides, free fatty acids, or a combination of triglycerides and free fatty acids.

In the illustrated embodiment, the natural oil feed 14 is delivered to a deoxygenation unit 16 which also receives a hydrogen feed 18. In the deoxygenation unit 16, the triglycerides and fatty acids in the feed 14 are deoxygenated. Structurally, triglycerides are formed by three, typically different, fatty acid molecules that are bonded together with a glycerol bridge. The glycerol molecule includes three hydroxyl groups (HO—) and each fatty acid molecule has a carboxyl group (COOH). In triglycerides, the hydroxyl groups of the glycerol join the carboxyl groups of the fatty acids to form ester bonds. Therefore, during deoxygenation, the fatty acids are freed from the triglyceride structure and are converted into normal paraffins. The glycerol is converted into propane, and the oxygen in the hydroxyl and carboxyl groups is converted into either water or carbon dioxide. The deoxygenation reaction for fatty acids and triglycerides are respectively illustrated as:

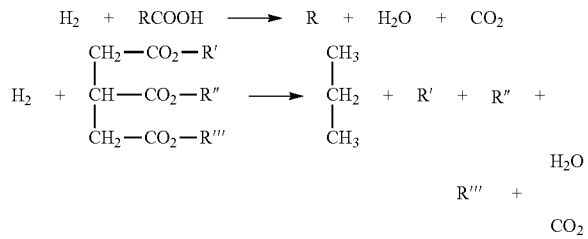

During the deoxygenation reaction, the length of a paraffin chain R″ created will vary by a value of one depending on the exact reaction pathway. For instance, if carbon dioxide is formed, then the chain will have one fewer carbon than the fatty acid source (R″). If water is formed, then the chain will match the length of the R″ chain in the fatty acid source. Typically, water and carbon dioxide are formed in roughly equal amounts, such that equal amounts of $C_n$, paraffins and $C_{n-1}$ paraffins are formed.

In FIG. 1, a deoxygenated stream 20 containing normal paraffins, water, carbon dioxide and propane exits the deoxygenation unit 16 and is fed to a separator 22. The separator 22 may be a multi-stage fractionation unit, distillation system or similar known apparatus. In any event, the separator 22 removes the water, carbon dioxide, and propane from the deoxygenated stream 20. Further, the separator 22 may provide a first portion of paraffins 23 and a second portion of paraffins 21. In certain embodiments, the first portion of paraffins 23 has carbon chain lengths of $C_{10}$ to $C_{14}$. In other embodiments, the first portion of paraffins 23 has carbon chain lengths having a lower limit of $C_L$, where L is an integer from four (4) to thirty-one (31), and an upper limit of $C_U$, where U is an integer from five (5) to thirty-two (32). The second portion of paraffins 21 may have carbon chains shorter than, longer than, or a combination of shorter and longer than, the chains of the first portion of paraffins 23. In a preferred embodiment, the first portion of paraffins 23 comprises paraffins with $C_{10}$ to $C_{13}$ chains and the second portion of paraffins 21 comprises paraffins with $C_{17}$ to $C_{18}$ chains.

As shown in FIG. 1, the first portion of paraffins 23 is introduced to a hydrocracking unit 24. The hydrocracking unit 24 preferably holds a mild hydrocracking catalyst, such that results in lower isoparaffin production. Hydrocracking of the paraffins 23 results in a stream of normal and lightly branched paraffins 25 and an isoparaffin stream 26. Preferably, the normal and lightly branched paraffins 25 are in the $C_9$ to $C_{14}$ range. As shown, the normal and lightly branched paraffin stream 25 is fed to an alkylbenzene production zone 28. Specifically, the normal and lightly branched paraffin stream 25 is fed into a dehydrogenation unit 30 in the alkylbenzene production unit 28. In the dehydrogenation unit 30, the normal and lightly branched paraffin stream 25 is dehydrogenated into mono-olefins of the same carbon numbers as the paraffin stream 25. Typically, dehydrogenation occurs through known catalytic processes, such as the commercially popular Pacol process. Di-olefins (i.e., dienes) and aromatics are also produced as an undesired result of the dehydrogenation reactions as expressed in the following equations:

Mono-olefin formation: $C_XH_{2X+2} \rightarrow C_XH_{2X}+H_2$

Di-olefin formation: $C_XH_{2X} \rightarrow C_XH_{2X-2}+H_2$

Aromatic formation: $C_XH_{2X-2} \rightarrow C_XH_{2X-6}+2H_2$

In FIG. 1, a dehydrogenated stream 32 exits the dehydrogenation unit 30 comprising mono-olefins and hydrogen, as well as some di-olefins and aromatics. The dehydrogenated stream 32 is delivered to a phase separator 34 for removing the hydrogen from the dehydrogenated stream 32. As shown, the hydrogen exits the phase separator 34 in a recycle stream of hydrogen 36 that can be added to the hydrogen feed 18 to support the deoxygenation process upstream.

At the phase separator 34, a liquid stream 38 is formed and comprises the mono-olefins and any di-olefins and aromatics formed during dehydrogenation. The liquid stream 38 exits the phase separator 34 and enters a selective hydrogenation unit 40, such as a DeFine reactor. The hydrogenation unit 40 selectively hydrogenates at least a portion of the di-olefins in the liquid stream 38 to form additional mono-olefins. As a result, an enhanced stream 42 is formed with an increased mono-olefin concentration.

As shown, the enhanced stream 42 passes from the hydrogenation unit 40 to a lights separator 44, such as a stripper column, which removes a light end stream 46 containing any lights, such as butane, propane, ethane and methane, that resulted from cracking or other reactions during upstream processing. With the light ends 46 removed, stream 48 is formed and may be delivered to an aromatic removal apparatus 50, such as a Pacol Enhancement Process (PEP) unit available from UOP. As indicated by its name, the aromatic removal apparatus 50 removes aromatics from the stream 48 and forms a stream of mono-olefins 52.

In FIG. 1, the stream of mono-olefins 52 and a stream of benzene 54 are fed into an alkylation unit 56. The alkylation unit 56 holds a catalyst 58, such as a solid acid catalyst, that supports alkylation of the benzene 54 with the mono-olefins 52. Hydrogen fluoride (HF) and aluminum chloride ($AlCl_3$) are two major catalysts in commercial use for the alkylation of benzene with linear mono-olefins and may be used in the alkylation unit 56. As a result of alkylation, alkylbenzene, typically called linear alkylbenzene (LAB), is formed according to the reaction:

$C_6H_6 + C_XH_{2X} \rightarrow C_6H_5C_XH_{2X+1}$ and is present in an alkylation effluent 60.

To optimize the alkylation process, surplus amounts of benzene 54 are supplied to the alkylation unit 56. Therefore, the alkylation effluent 60 exiting the alkylation unit 56 contains alkylbenzene and unreacted benzene. Further the alkylation effluent 60 may also include some unreacted paraffins. In FIG. 1, the alkylation effluent 60 is passed to a benzene separation unit 62, such as a fractionation column, for separating the unreacted benzene from the alkylation effluent 60. This unreacted benzene exits the benzene separation unit 62 in a benzene recycle stream 64 that is delivered back into the alkylation unit 56 to reduce the volume of fresh benzene needed in stream 54.

As shown, a benzene-stripped stream 66 exits the benzene separation unit 62 and enters a paraffinic separation unit 68, such as a fractionation column. In the paraffinic separation unit 68, unreacted paraffins are removed from the benzene-stripped stream 66 in a recycle paraffin stream 70, and are routed to and mixed with the paraffin stream 25 before dehydrogenation as described above.

Further, an alkylbenzene stream 72 is separated by the paraffinic separation unit 68 and is fed to an alkylate separation unit 74. The alkylate separation unit 74, which may be, for example, a multi-column fractionation system, separates a heavy alkylate bottoms stream 76 from the alkylbenzene stream 72.

As a result of the post-alkylation separation processes, the linear alkylbenzene product 12 is isolated and exits the apparatus 10. It is noted that such separation processes are not necessary in all embodiments in order to isolate the alkylbenzene product 12. For instance, the alkylbenzene product 12 may be desired to have a wide range of carbon chain lengths and not require any fractionation to eliminate carbon chains longer than desired, i.e., heavies or carbon chains shorter than desired, i.e., lights. Further, the feed 14 may be of sufficient quality that no fractionation is necessary despite the desired chain length range.

In certain embodiments, the feed 14 includes oils substantially having $C_{22}$ fatty acids. In other certain embodiments, the feed 14 is substantially homogeneous and comprises free fatty acids within a desired range. For instance, the feed may be palm fatty acid distillate (PFAD). Alternatively, the feed 14 may comprise triglycerides and free fatty acids that all have carbon chain lengths appropriate for a desired alkylbenzene product 12.

In certain embodiments, the natural oil source is castor, and the feed 14 comprises castor oils. Castor oils consist essentially of $C_{18}$ fatty acids with an additional, internal hydroxyl groups at the carbon-12 position. For instance, the structure of a castor oil triglyceride is:

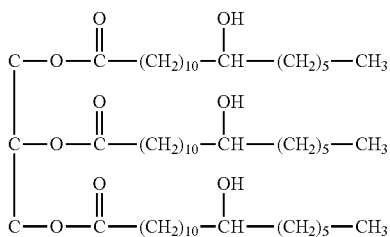

During deoxygenation of a feed 14 comprising castor oil, it has been found that some portion of the carbon chains are cleaved at the carbon-12 position. Thus, deoxygenation creates a group of lighter paraffins having $C_{10}$ to $C_{11}$ chains resulting from cleavage during deoxygenation, and a group of non-cleaved heavier paraffins having $C_{17}$ to $C_{18}$ chains. The lighter paraffins may form the first portion of paraffins 23 and the heavier paraffins may form the second portion of paraffins 21. It should be noted that while castor oil is shown as an example of an oil with an additional internal hydroxyl group, others may exist. Also, it may be desirable to engineer genetically modified organisms to produce such oils by design. As such, any oil with an internal hydroxyl group may be a desirable feed oil.

As shown in FIG. 1, the second portion of paraffins 21 and the isoparaffin stream 26 are co-fed to a system 80 for producing biofuel 13 such as diesel or jet fuel, such as synthetic paraffinic kerosene (SPK). Typically, no further deoxygenation is needed in the biofuel production system 80. Rather, in the system 80, the second portion of paraffins 21 are typically isomerized in an isomerization unit 82 or cracked in a cracking unit 84 to create the isoparaffins of equal or lighter molecular weight than the second portion of paraffins 21. Hydrogen may be separated out from the resulting biofuel 13 to form a hydrogen stream 86 that is recycled to the deoxygenation unit 16. While shown feeding the deoxygenation unit 16 directly, the hydrogen stream 86 could be fed to hydrogen feed 18. In particular, in certain embodiments, the isoparaffin stream 26 is in the naphtha range, and system 80 includes a reformer that produces hydrogen 86 from the isoparaffin stream 26.

In order to create biodiesel, the biofuel production system 80 primarily isomerizes the second portion of paraffins 21 with minimal cracking. For the production of biojet or green jet fuel, some cracking is performed in order to obtain smaller molecules (with reduced molecular weight) to the properties required by jet specifications.

While at least one exemplary embodiment has been presented in the foregoing Detailed Description, it should be appreciated that a vast number of variations exist. It should also be appreciated that the exemplary embodiment or exemplary embodiments are only examples, and are not intended to limit the scope, applicability, or configuration of the invention in any way. Rather, the foregoing Detailed Description will provide those skilled in the art with a convenient road map for implementing an exemplary embodiment of the invention, it being understood that various changes may be made in the function and arrangement of elements described in an exemplary embodiment without departing from the scope of the invention as set forth in the appended Claims and their legal equivalents.

What is claimed is:

1. A method for co-production of an alkylbenzene product and a biofuel from a natural oil comprising:
   deoxygenating the natural oil to form paraffins;
   hydrocracking a first portion of the paraffins to form a first stream of normal or lightly branched paraffins in the $C_9$ to $C_{14}$ range and a second stream of isoparaffins;
   dehydrogenating the first stream to provide mono-olefins;
   alkylating benzene with the mono-olefins under alkylation conditions to provide an alkylation effluent comprising alkylbenzenes and benzene;
   isolating the alkylbenzenes to provide the alkylbenzene product; and
   isomerizing a second portion of the paraffins and the second stream of isoparaffins to form biofuel.

2. The method of claim 1 wherein the second stream of isoparaffins is in the naphtha range, and wherein during processing of the second stream of isoparaffins, hydrogen is produced and is recycled to support deoxygenating the natural oil.

3. The method of claim 1 wherein a hydrogen stream results from dehydrogenating the first stream, and wherein the method further comprises recycling the hydrogen stream to support the deoxygenating step.

4. The method of claim 1 wherein di-olefins are also produced by dehydrogenating the first stream, and wherein the method further comprises selectively hydrogenating the di-olefins to form additional mono-olefins.

5. The method of claim 4 further comprising removing aromatics produced by the dehydrogenating step from the mono-olefins before alkylating.

6. The method of claim 1 wherein the natural oil comprises a first plurality of fatty acids having a first range of chain lengths and a second plurality of fatty acids having a second range of chain lengths; wherein first chain length paraffins and second chain length paraffins are formed by deoxygenating the natural oils; wherein the first portion of the paraffins comprises the first chain length paraffins; and wherein the second portion of the paraffins comprises the second chain length paraffins; the method further comprising:
fractionating the paraffins to separate the first portion of paraffins from the second portion of paraffins before hydrocracking.

7. The method of claim 1 wherein isolating provides the alkylbenzene product comprising alkylbenzenes having $C_8$ to $C_{28}$ chains.

8. The method of claim 1 wherein the natural oil comprises $C_{22}$ fatty acids, and wherein deoxygenating the natural oil causes cleaving and provides the portion of the paraffins and the second portion of the paraffins.

9. A method for co-production of an alkylbenzene product and a biofuel from natural oil source triglycerides comprising:
deoxygenating the triglycerides to form a deoxygenated product comprising water, carbon dioxide, propane, a first portion of paraffins, and a second portion of paraffins;
fractionating the deoxygenated product to separate a first stream of paraffins and a second stream of paraffins;
hydrocracking the first stream of paraffins to form a normal paraffin stream and an isoparaffin stream;
dehydrogenating the normal paraffin stream to provide mono-olefins;
alkylating benzene with the mono-olefins under alkylation conditions to provide an alkylation effluent comprising alkylbenzenes and benzene;
isolating the alkylbenzenes to provide the alkylbenzene product; and
isomerizing the second stream of paraffins and the isoparaffin stream to form biofuel.

10. The method of claim 9 wherein the biofuel is synthetic paraffinic kerosene.

11. The method of claim 9 wherein a hydrogen stream results from dehydrogenating the normal paraffin stream, and wherein the method further comprises recycling the hydrogen stream to support the deoxygenating step.

12. The method of claim 9 wherein di-olefins are also produced by dehydrogenating the normal paraffin stream, the method further comprising selectively hydrogenating the di-olefins to form additional mono-olefins for alkylating the benzene.

13. The method of claim 9 further comprising removing aromatics produced by the dehydrogenating step from the mono-olefins before alkylating.

14. The method of claim 9 wherein:
the natural oil source is castor oil;
the triglycerides consist essentially of $C_{18}$ fatty acids with hydroxyl groups at the carbon-12 position; and
deoxygenating the triglycerides causes cleaving and provides the first stream of paraffins and the second stream of paraffins.

15. The method of claim 14 wherein the first stream of paraffins have $C_{10}$ to $C_{11}$ chains.

16. The method of claim 15 wherein the second stream of paraffins have $C_{17}$ to $C_{18}$ chains.

17. A method for co-production of an alkylbenzene product and biofuel from a natural oil comprising:
deoxygenating the natural oil with hydrogen to form a stream comprising paraffins;
hydrocracking the paraffins to form a normal paraffin stream and an isoparaffin stream;
dehydrogenating the normal paraffin stream to provide mono-olefins and hydrogen;
recycling the hydrogen to support deoxygenation of the natural oil;
alkylating benzene with the mono-olefins under alkylation conditions to provide an alkylation effluent comprising alkylbenzenes and benzene;
isolating the alkylbenzenes to provide the alkylbenzene product; and
isomerizing the isoparaffin stream to form biofuel.

18. The method of claim 17 wherein the biofuel is synthetic paraffinic kerosene.

19. The method of claim 17 wherein a hydrogen stream results from dehydrogenating the normal paraffin stream, and wherein the method further comprises recycling the hydrogen stream to support the deoxygenating step.

* * * * *